United States Patent
Paul et al.

(10) Patent No.: US 7,252,683 B2
(45) Date of Patent: Aug. 7, 2007

(54) INTRAOCULAR LENS FOR INHIBITING CELL GROWTH AND REDUCING GLARE

(75) Inventors: Marlene L. Paul, Laguna Niguel, CA (US); Daniel G. Brady, San Juan Capistrano, CA (US); Jim Deacon, Golita, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 20 days.

(21) Appl. No.: 10/245,920

(22) Filed: Sep. 18, 2002

(65) Prior Publication Data
US 2003/0114926 A1 Jun. 19, 2003

Related U.S. Application Data

(63) Continuation of application No. 09/507,602, filed on Feb. 18, 2000, now Pat. No. 6,468,306, which is a continuation of application No. 09/448,713, filed on Nov. 24, 1999, now abandoned, which is a continuation-in-part of application No. 09/086,882, filed on May 29, 1998, now Pat. No. 6,162,249.

(51) Int. Cl.
*A61F 2/16* (2006.01)
(52) U.S. Cl. ..................... 623/6.16; 623/6.17
(58) Field of Classification Search ............. 623/6.11, 623/6.16, 6.17, FOR. 105, 6.28
See application file for complete search history.

(56) References Cited

U.S. PATENT DOCUMENTS

| | | | |
|---|---|---|---|
| 4,743,254 A | * | 5/1988 | Davenport ............... 623/6.17 |
| 4,842,782 A | | 6/1989 | Portney et al. |
| 5,192,318 A | * | 3/1993 | Schneider et al. ......... 623/6.28 |
| 5,549,670 A | * | 8/1996 | Young et al. ............. 623/6.16 |
| 5,674,283 A | * | 10/1997 | Stoy ......................... 623/5.11 |

FOREIGN PATENT DOCUMENTS

| | | | |
|---|---|---|---|
| DE | 32 46 306 A1 | * | 6/1984 |
| EP | 0 246 754 A1 | * | 11/1987 |
| WO | WO 94/18908 | | 9/1994 |
| WO | WO 96/35397 | | 11/1996 |
| WO | WO 97/33536 A1 | * | 9/1997 |

OTHER PUBLICATIONS

Nishi et al., Ophthalmic Surg Lasers 1998;29:587-593.*

* cited by examiner

*Primary Examiner*—Dave Willse (57) ABSTRACT

An intraocular lens implantable in an eye includes an optic for placement in the capsular bag of the eye and for directing light toward the retina of the eye. The optic has a central optical axis, an anterior face, an opposing posterior face and a peripheral edge between the faces. The peripheral edge has one or more curved or angled surfaces that reduce glare within the IOL. For instance, a rounded transition surface on the anterior side of the peripheral edge diffuses the intensity of reflected light, or a particular arrangement of straight edge surfaces refracts the light so as not to reflect, or does not reflect at all. The intersection of the peripheral edge and at least one of the anterior face and the posterior face, preferably both of such faces, forms a peripheral corner located at a discontinuity between the peripheral edge and the intersecting face or faces. The present IOLs inhibit cell growth from the eye in front of or in back of the optic and reduce glare obtained in the eye in which the IOL is located.

6 Claims, 8 Drawing Sheets

INTRAOCULAR LENS FOR INHIBITING CELL GROWTH AND REDUCING GLARE

RELATED APPLICATION

The present application is a continuation of application Ser. No. 09/507,602, filed Feb. 18, 2000, now U.S. Pat. No. 6,468,306, issued Oct. 22, 2002, which is a continuation of application Ser. No. 09/448,713, filed Nov. 24, 1999, now abandoned, which is a continuation-in-part of application Ser. No. 09/086,882, filed May 29, 1998, now U.S. Pat. No. 6,162,249, issued Dec. 19, 2000. The disclosure of the application and each of the patents is incorporated in its entirety by reference herein.

BACKGROUND OF THE INVENTION

This invention relates to intraocular lenses (IOLs) and, more particularly, to IOLs which inhibit migration or growth of cells from the eye onto the IOL and reduce glare in the eye.

An intraocular lens is commonly used to replace the natural lens of a human eye when warranted by medical conditions. It is common practice to implant an IOL in a region of the eye known as the capsular bag or posterior capsule.

One potential concern with certain IOLs following implantation is that cells from the eye, particularly epithelial cells from the capsular bag, tend to grow in front of and/or in back of the optic of the IOL. This tends to block the optic of the IOL and to impair vision.

A common treatment for this condition is to use a laser to destroy the cells and a central region of the capsular bag. Although this treatment is effective, the laser is expensive and is not available throughout the world. There is also cost associated with the laser treatment as well as some patient inconvenience and risk of complications. Finally, the laser treatment may affect the performance of some IOLs.

Another potential concern after certain IOLs are implanted has to do with glare caused by light reflecting off of the IOLs, in particular, the edges of IOLs. Such glare can be an annoyance to the patient and may even lead to removal and replacement of the IOL.

It would be advantageous to provide IOLs which inhibit growth of cells from the eye onto the IOLs and/or which reduce glare caused by the IOLs in the eye.

SUMMARY OF THE INVENTION

New IOLs have been discovered. Such IOLs are effective to inhibit cell growth, in particular epithelial cell growth, from the eye onto the optic of the IOLs. The IOLs are structured so as to reduce glare, in particular edge glare, in the eye resulting from the presence of the IOL. The present IOLs are straightforward in design and construction, are easily manufactured, can be implanted, or inserted in the eye using conventional techniques, and are effective and produce substantial benefits in use in the eye.

In one broad aspect of the present invention, the present IOLs are implantable in the eye and comprise an optic having a central optical axis, an anterior face, an opposing posterior face and a peripheral edge or edge surface between the faces. The optic is adapted for placement in the capsular bag of the eye and for directing light toward the retina of the eye. In a very useful embodiment, the IOLs further comprise at least one fixation member, preferably two fixation members, and more preferably two elongated fixation members, coupled to the optic for use in fixing the IOLs in the eye.

In a preferred aspect, the present invention provides a reduced-glare intraocular lens implantable in the eye and including an optic adapted for placement in the capsular bag of the eye for directing light toward the retina of the eye. The optic has a central optical axis, an anterior face, an opposing posterior face, and a peripheral edge. The peripheral edge has a least one surface with a linear cross-sectional configuration that is oriented other than parallel to the central optical axis. Further, the peripheral edge and the anterior face, and/or the peripheral edge and the posterior face, intersect to form at least one peripheral edge corner located at a discontinuity between the peripheral edge and the intersecting anterior or posterior face. The peripheral edge may also include a rounded transition surface on its anterior side, wherein the peripheral edge corner is provided only between the peripheral edge and intersecting posterior face. The peripheral edge may also include two linear surfaces angled with respect to one another, wherein the other linear surface may be oriented parallel to the optical axis.

In another aspect of present invention, a reduced-glare intraocular lens implantable in an eye comprises an optic adapted for placement in the capsular bag of the eye and for directing light toward the retina of the eye. The optic has a central optical axis, an anterior face, and a posterior face. An outer edge of the optic is defined by a peripheral edge that includes, in cross-section, a linear surface that is non-parallel with respect to the optical axis and a posterior corner defining the posterior limit of the peripheral edge. Advantageously, cell growth from the eye in front of or in back of the optic is more inhibited relative to a substantially identical intraocular lens without the posterior corner, and reduced glare is obtained in the eye relative to a substantially identical intraocular lens having a peripheral linear surface that is parallel to the central optical axis. The optic may also include a convex surface on the peripheral edge defining a transition surface between the anterior face and the linear surface. A second linear surface that is parallel with respect to the optical axis may also be provided. In addition, the optic may include first and second linear surfaces, wherein the first linear surface is anteriorly-facing and second linear surface is parallel with respect to the optical axis.

In still a further embodiment of the present invention, an intraocular lens implantable in an eye includes an optic adapted for placement in the capsular bag of the eye and for directing light toward the retina of the eye. The optic includes a peripheral edge extending between an anterior face and a posterior face consisting only of a conical surface. The conical surface may be posteriorly-facing, wherein the conical surface is sufficiently angled with respect to the optical axis so as to increase transmission of light from the optic through the conical surface relative to a substantially identical intraocular lens with a peripheral edge consisting only of a surface parallel to the optical axis. Alternatively, a peripheral land extends between the anterior face and conical surface, wherein the conical surface is generally posteriorly-facing and wherein the conical surface and the peripheral land adjacent the conical surface define an acute included angle. In a still further form, the conical surface may be anteriorly-facing, wherein the conical surface is sufficiently angled with respect to the optical axis so as to decrease the probability of light internal to the optic contacting the conical surface relative to a substantially identical intraocular lens with a peripheral edge consisting only of a surface parallel to the optical axis.

Another aspect of present invention is an intraocular lens including an optic defining a central optical axis, an anterior face, and a posterior face. A peripheral edge extending between the anterior face and the posterior face includes, in cross-section, a linear edge surface terminating at its anterior side in an anterior edge corner. An anterior land adjacent the anterior edge corner, wherein the linear edge surface and the anterior land define an acute included angle so as to increase transmission of light from the optic through the conical surface relative to a substantially identical intraocular lens with a linear edge surface and anterior land that define an included angle of 90° or more.

In a still further form, the present invention provides an intraocular lens having optic defining optical axis, an anterior face, and a posterior face. A peripheral edge stands between the anterior face and posterior face and includes, in cross-section, at least two linear edge surfaces that are not parallel to the optical axis. The two linear edge surfaces may be angled radially inwardly toward each other to meet an apex and together define a groove. Further, a plurality of such grooves may be provided by adjoining linear edge surfaces. A rounded transition surface extending between an anteriorly-facing edge surface and the anterior face of the optic may also be provided.

The peripheral edge of the present IOLs may have a substantially continuous curved configuration in the direction between the anterior and posterior faces of the optic, that is between the faces in a cross-sectional plane including the optical axis. Indeed, the entire peripheral edge may have a substantially continuous curved configuration in the direction between the anterior and posterior faces of the optic.

The peripheral edge of the present IOLs may have a curved surface, a flat surface that is either parallel to the optical axis or not, or a combination of flat and/or curved surfaces. For example, if a portion of the peripheral edge has a substantially continuous curved configuration, another portion, for example, the remaining portion, of the peripheral edge preferably has a linear configuration in the direction between the anterior and posterior faces of the optic which is not parallel to the optical axis.

The present IOLs preferably provide reduced glare in the eye relative to the glare obtained with a substantially identical IOL having a peripheral edge parallel (flat) to the central optical axis in the direction between the faces of the optic. One or more of at least part of the peripheral edge, a portion of the anterior face near the peripheral edge and a portion of the portion face near the peripheral edge may be at least partially opaque to the transmission of light, which opacity is effective in reducing glare. Such opacity can be achieved in any suitable manner, for example, by providing "frosting" or physically or chemically roughening selected portions of the optic.

In addition, the intersection of the peripheral edge and at least one or both of the anterior face and the posterior face forms a peripheral corner or corner edge located at a discontinuity between the peripheral edge and the intersecting face. Such peripheral corner, which may be considered a sharp, abrupt or angled peripheral corner, is effective in inhibiting migration or growth of cells from the eye onto the IOL. Preferably, the present IOLs, with one or two such angled peripheral corners, provide that cell growth from the eye in front of or in back of the optic is more inhibited relative to a substantially identical IOL without the sharp, abrupt or angled peripheral corner or corners.

The peripheral edge and the intersecting face or faces intersect at an angle or angles, preferably in a range of about 45° to about 135°, more preferably in a range of about 60° to about 120°. In one embodiment, an obtuse angle (that is greater than 90° and less than 180°) of intersection is provided. Such angles of intersection are very effective in facilitating the inhibition of cell migration or growth onto and/or over the anterior face and/or posterior face of the optic of the present IOL.

In one very useful embodiment, at least one, conceivably both, of the anterior face and the posterior face has a peripheral region extending from the peripheral edge toward the central optical axis. The peripheral region or regions preferably are substantially planar, and may or may not be substantially perpendicular to the central optical axis. Preferably, only the anterior face has a peripheral region extending from the peripheral edge toward the central optical axis which is substantially planar, more preferably substantially perpendicular to the central optical axis. The peripheral region preferably has a radial dimension of at least about 0.1 mm, and more preferably no greater than about 2 mm.

The dimension of the optic parallel to the central optical axis between the anterior face and the posterior face preferably is smaller at or near the peripheral edge, for example, at the peripheral region or regions, than at the central optical axis.

In one embodiment, at least a part or a portion of the peripheral edge surface of the optic is generally convex relative to the central optical axis. Alternately, at least a part or a portion of the peripheral edge surface of the optic is generally concave relative to the central optical axis. In a particularly useful embodiment, a first portion of the peripheral edge surface is generally convex relative to the central optical axis and a second portion of the peripheral edge surface is generally concave relative to the optical axis.

Preferably, the peripheral edge and/or the peripheral region or regions circumscribe the central optical axis. The anterior face and the posterior face preferably are both generally circular in configuration, although other configurations, such as oval, elliptical and the like, may be employed. At least one of the anterior and posterior faces has an additional region, located radially inwardly of the peripheral region, which is other than substantially planar.

Each and every combination of two or more features described herein is included within the scope of the present invention provided that such features are not mutually inconsistent.

The invention, together with additional features and advantages thereof, may best be understood by reference to the following description taken in connection with the accompanying illustrative drawings in which like parts bear like reference numerals.

BRIEF DESCRIPTION OF THE DRAWINGS

FIG. 14b is an elevational view of a peripheral edge region of the IOL of FIG. 14a.

DESCRIPTION OF THE PREFERRED EMBODIMENTS

Figure 1:
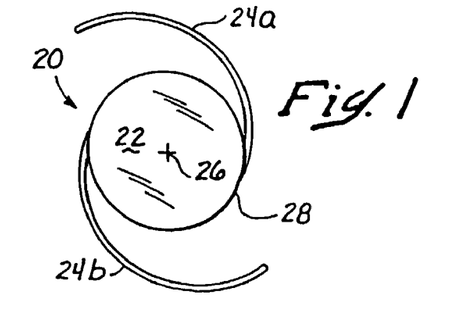
FIG. 1 is a plan view of one form of intraocular lens (IOL) constructed in accordance with the teachings of present invention.

FIG. 1 shows an IOL 20 which generally comprises an optic 22 and fixation members 24a and 24b. In this embodiment, the optic 22 may be considered as effective for focusing light on or near the retina of the eye. Optical axis 26 passes through the center of optic 22 in a direction generally transverse to the plane of the optic.

In this embodiment, the optic 22 is circular in plan and bi-convex approaching the optical axis 26. However, this configuration is merely illustrative as other configurations and shapes may be employed. The optic 22 may be constructed of any of the commonly employed materials used for rigid optics, such as polymethylmethacrylate (PMMA), or commonly employed materials used for resiliently deformable optics, such as silicone polymeric materials, acrylic polymeric materials, hydrogel-forming polymeric materials, mixtures thereof and the like.

The fixation members 24a and 24b in this embodiment are generally C-shaped and are integral with the optic 22. However, this is purely illustrative of the fixation members 24a and 24b as the fixation members may be of other configurations and/or may be separate members affixed to the optic 22 in any of a variety of conventional ways. Stated another way, the IOLs of the present invention may consist of one piece, with unitary optic and fixation members, or may be three or more pieces, with two or more fixation members connected to the optic. IOL 20 can be produced using conventional techniques well-known in the art.

Unless expressly described hereinafter, the general structural characteristics of IOL 20 apply to the other IOLs noted herein.

Figure 2:
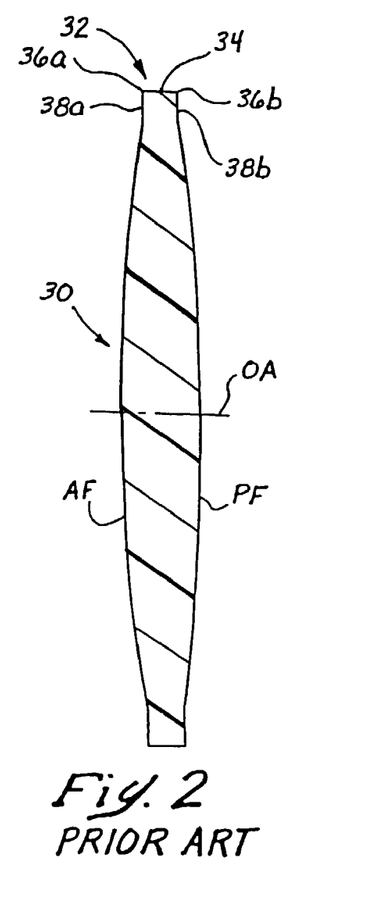
FIG. 2 is a cross-sectional view of an optic of a prior art IOL.

FIG. 2 illustrates an optic 30 of an IOL of the prior art having an optical axis OA, a convex anterior face AF, a convex posterior face PF, and a peripheral edge 32. The peripheral edge 32 is typically circular and has a constant cross-section circumscribing the optic 30. The optic 30 illustrated is of the square-cornered variety which provides some inhibition of cell growth onto the optic 30, a condition known as posterior capsule opacification (PCO). The peripheral edge 32 comprises an edge surface 34 that is parallel to the optical axis OA, and both anterior and posterior edge corners 36a, 36b, respectively. In addition, anterior and posterior lands 38a, 38b, extend between the anterior face AF and posterior face PF and respective edge corner 36a or 36b. Both the anterior and posterior lands 38a, 38b extend substantially perpendicularly with respect to the optical axis OA. Because of the parallel edge surface 34, the prior art optic 30 does not provide reduced edge glare as do the IOLs in accordance with the present invention.

In the present application, the terms anterior and posterior are used in their conventional sense; anterior refers to the front side of the eye, while posterior refers to the rear side. A number of surfaces of the intraocular lens of present invention are denoted either "anteriorly-facing" or "posteriorly-facing" to indicate their orientation with respect to the optical axis of the lens. For purpose of explanation, a surface that is parallel to the optical axis is neither anteriorly-facing or posteriorly-facing. A surface that is even slightly angled in one direction or the other can be identified with either the anterior or posterior side of the lens, depending on which side that surface faces.

Figure 3:
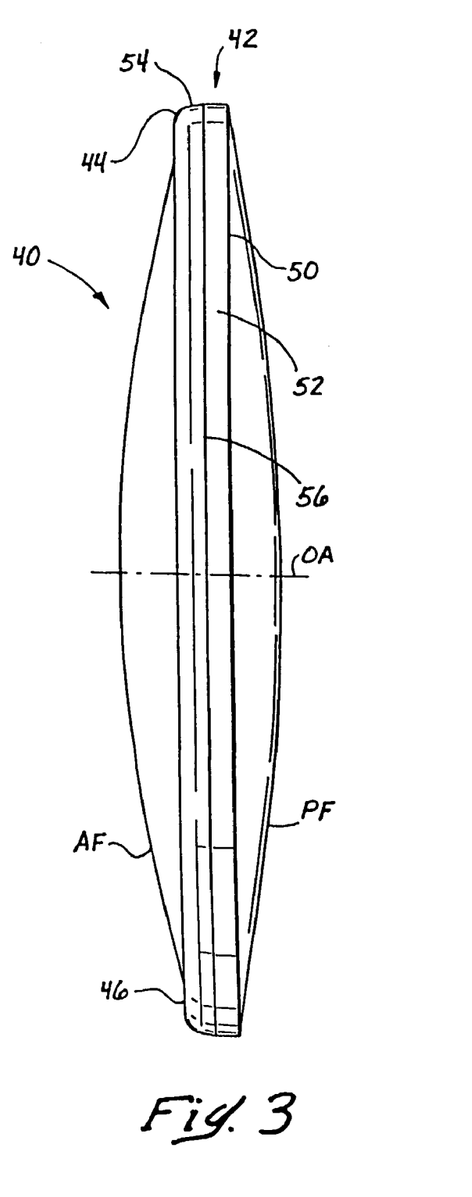
FIG. 3 is an elevational view of an optic of an exemplary embodiment of an IOL of the present invention having a medium diopter value.

FIG. 3 illustrates an optic 40 of an IOL of the present invention having an advantageous peripheral edge 42. The optic 40 defines an optical axis OA, a convex anterior face AF, and a convex posterior face PF. The peripheral edge 42 is desirably circular in shape, and has a constant cross-section circumscribing the optic 40. However, it should be understood by those skilled in the art that the peripheral edge 42 may not extend completely around the optic 40, and may be interrupted by alternative peripheral edge configurations, including combinations of peripheral edge configurations in accordance with the present invention.

The optic 40 is shown in elevational view to better illustrate the peripheral edge 42 in relation to the convex anterior face AF and posterior face PF. On the anterior side, the peripheral edge 42 includes a curved or rounded transition surface 44 leading to an anterior peripheral land or region 46 that is desirably linear and substantially perpendicular to the optical axis OA. On the posterior side, a discontinuous posterior edge corner 50 separates the peripheral edge 42 from the posterior face PF, with no peripheral land. The edge corner 50 defines the posterior limit of the peripheral edge 42. The peripheral edge 42 further comprises an edge surface 52 that is linear and substantially parallel to the optical axis OA adjacent the posterior edge corner 50, and an anteriorly-facing edge surface 54 that is linear and non-parallel to the optical axis OA adjacent the rounded transition surface 44. A shallow corner or discontinuity 56 separates the parallel edge surface 52 from the non-parallel edge surface 54.

In this respect, the term discontinuity refers to a transition between two peripheral edge surfaces that is visible as a corner or peripheral line on the optic. Of course, all corners ultimately have a radius, but discontinuity in this regard pertains only to a corner that is visible as a discrete line as opposed to a more rounded region. In turn, "visible" in this regard refers to visible as seen by the naked eye, or with the assistance of certain low-power magnification devices, such as an ocular. Another way to define corners in the presence sense is the intersection between two linear surfaces, at least with respect to the magnification shown in the drawings of the present application. Still another way to look at the effect of a discontinuity at the corner of the peripheral edge is that cell growth from the eye in front of or in back of the optic is more inhibited relative to a substantially identical intraocular lens without the discontinuity.

As used herein, the term "linear," used to refer to various edge surfaces, is in all cases as viewed through the cross-section of the particular edge. That is, the lenses of the present invention are generally circular, and the peripheral edges thus defined circular surfaces of revolution. A linear cross-sectional edge can therefore defined a cylinder, or a conical surface. If the edge is parallel to the optical axis, the surface is cylindrical. On the other hand, if the surface is non-parallel with respect to the optical axis, the surface is conical. Therefore, a linear, non-parallel edge surface is conical, at least for a portion of the peripheral edge. It should be noted that, as mentioned above, the edge geometry around the periphery of any particular lens of the present invention may not be constant, and the edge surfaces disclosed herein should not be construed as necessarily extending in a constant configuration around the entire periphery of the lens.

Although the anterior peripheral land or region 46 is shown as being linear and substantially perpendicular to the optical axis OA, other configurations are contemplated. For example, the peripheral land 46 could be other than linear, i.e., convex or concave with respect to a plane through the medial plane of the optic. Or, the peripheral land 46 could be angled toward or away from the anterior side. Further, there may be more than one surface defining the peripheral land 46, such as a curved and a linear surface.

Figures 4, 5:
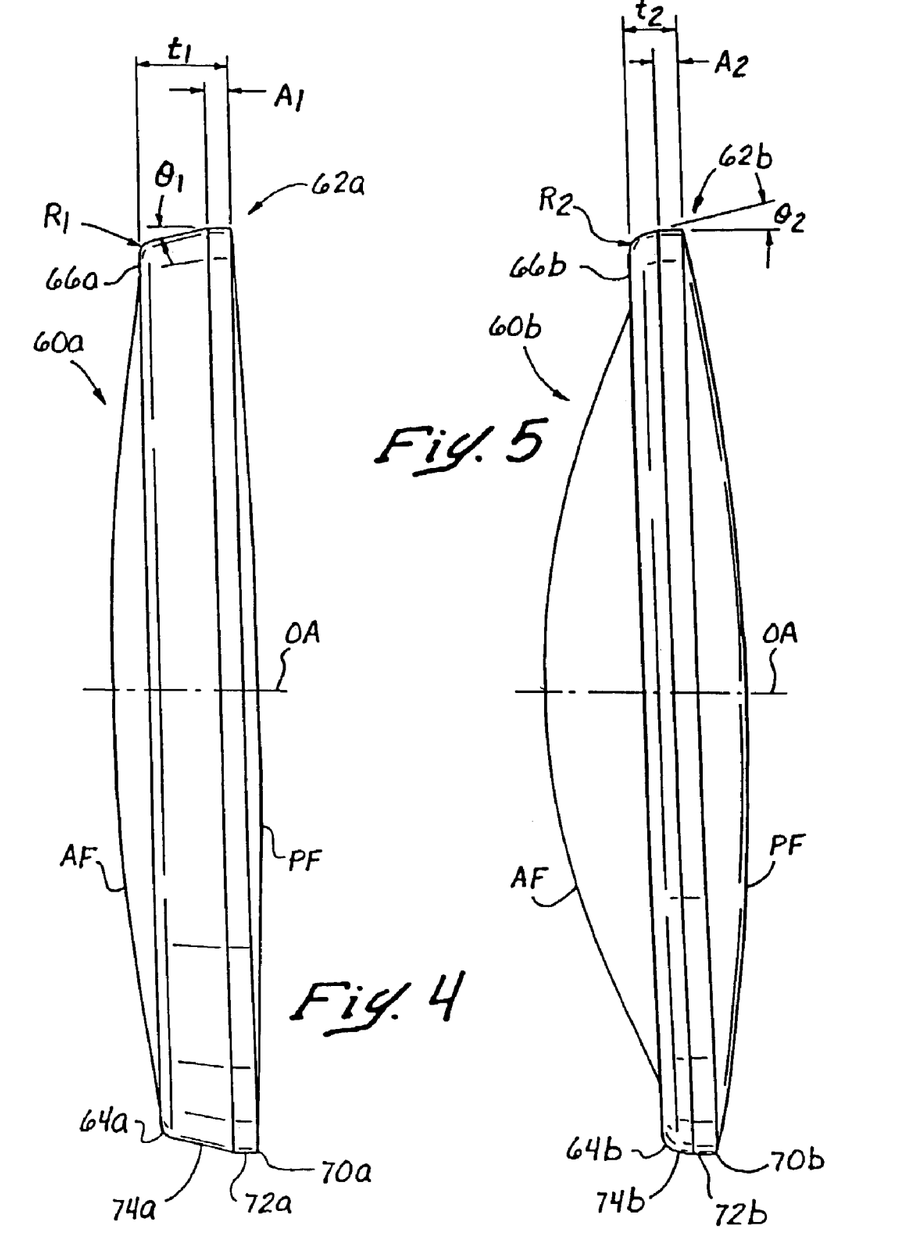
FIG. 4 is an elevational view of an optic of a further exemplary IOL of the present invention having a small diopter value.
FIG. 5 is an elevational view of an optic of a further exemplary IOL of the present invention having a large diopter value.

FIGS. 4 and 5 illustrate two further optics 60a and 60b that have substantially the same configuration as the optic 40 of FIG. 3. That is, both optics 60a and 60b have an optical axis OA, a convex anterior face AF, a convex posterior face PF, and a peripheral edge 62a, 62b, respectively. Each peripheral edge 62a, 62b, comprises, respectively, a rounded transition surface 64a, 64b, and anterior peripheral land 66a, 66b that is substantially perpendicular to the optical axis OA, a posterior edge corner 70a, 70b, an edge surface 72a, 72b that is substantially parallel to the optical axis OA, and an anteriorly-facing edge surface 74a, 74b that is non-parallel to the optical axis OA.

FIGS. 3, 4 and 5 illustrate optics of similar configuration that have different dimensions based on their different magnitude of optical correction, or diopter value. The optic 40 of FIG. 3 has an intermediate correction diopter value of 20, the optic 60a of FIG. 4 has a diopter value of 10, and the optic 60b of FIG. 5 has a diopter value of 30. These relative diopter values are reflected in the relative convexity of each. That is, the smallest diopter value optic 40 shown in FIG. 4 has relatively shallow convex anterior face AF and posterior face PF. In contrast, the larger diopter value optic 60b in FIG. 5 has a larger convexity for both the anterior face AF and posterior face PF.

Various dimensions for the respective peripheral edges of the exemplary optics shown in FIGS. 3–5 are also given in FIGS. 4 and 5. That is, the thickness of each peripheral edge is given as t, the thickness of the parallel edge surface is given as A, the angle of the non-parallel edge surface is given as $\theta$, and a radius of curvature of the transition surface is given as R.

The following tables provide exemplary values for these dimensions for the optics 60a and 60b of FIGS. 4 and 5. These dimensions are considered suitable for optics 60a and 60b that are made from silicone. It should be noted that the dimensions for the optic 40 of FIG. 3 are desirably approximately equal to those for the optic 60b of FIG. 5. It should also be noted that the following dimensions are believed to provide certain benefits as far as reducing glare and PCO in IOLs, although not all the dimensions have been selected for either of those particular purposes. For example, some of the dimensions may be desirable to facilitate manufacturing of the respective IOL.

Table I provides exemplary values for optics that are made from acrylic.

TABLE I

EXEMPLARY DIMENSIONS FOR SILICONE IOLs

| $T_1$ (in) | $t_2$ (in) | $A_1$ (in) | $A_2$ (in) | $\theta_1$ | $\theta_2$ | $R_1$ (in) | $R_2$ (in) |
|---|---|---|---|---|---|---|---|
| .023–.027 | .012–.014 | .002–.007 | .002–.007 | 13–17° | 13–17° | .001–.003 | .004–.006 |

Table II provides exemplary values for the same dimensions as shown in FIGS. 4–5, but for optics that are made from acrylic. In this case, the subscript "1" pertains to optics having a diopter value of 10, while the subscript "2" pertains to optics having a diopter value of either 20 or 30.

TABLE II

EXEMPLARY DIMENSIONS FOR ACRYLIC IOLs

| $t_1$ (in) | $t_2$ (in) | $A_1$ (in) | $A_2$ (in) | $\theta_1$ | $\theta_2$ | $R_1$ (in) | $R_2$ (in) |
|---|---|---|---|---|---|---|---|
| .015–.019 | .013–.017 | .002–.007 | .002–.007 | 13–17° | 13–17° | .004–.008 | .004–.008 |

As is apparent from FIGS. 3–5, the convexity of the various lenses along the optical axis OA increases with increasing diopter value (the posterior face and especially the anterior face are more highly convex). However, some surgeons prefer the intraocular lenses to have approximately the same volume or center thickness at the optical axis regardless of diopter power. This permits the surgeon to use the same surgical technique across the diopter range. Therefore, the present invention contemplates varying the overall diameter of the optic for different diopter values. That is, the center thickness of the intraocular lenses for different diopter values remains the same regardless of diameter. Therefore, the diameter of lenses having greater convexity should be reduced to reduce the center thickness, and the diameter of flatter lenses should be increased, both to an intermediate value. For example, the diameter of the lower diopter value optic 60a shown in FIG. 4 may be increased so that the center thickness is closer to the intermediate diopter value optic 40 shown in FIG. 3. Likewise, the diameter of the higher diopter value optic 60b shown in FIG. 5 may be decreased so that the center thickness is closer to the optic 40 shown in FIG. 3.

Therefore, the present invention contemplates a set of intraocular lenses having varying diopter values wherein the diameter of the optics varies generally inversely (although not necessarily linearly) with respect to the diopter value. In this way, a set of intraocular lenses having approximately the same center thickness can be provided to the surgeon to help make the implantation procedure more consistent and predictable. One example of a set of intraocular lenses may include the optics shown in FIGS. 3–5. The lower diopter lens 60a of FIG. 4 may have a diameter of approximately 6.25 mm, the intermediate diopter lens 40 of FIG. 3 may have a diameter of 6.0 mm, and the higher diopter lens 60b of FIG. 5 may have a diameter of 5.75 mm. Advantageously, an increased diameter for lower diopter lenses corresponds to human physiology. That is, people who require lower diopter lenses typically have larger eyes, while people requiring high diopters tend to have smaller eyes.

Figure 6:
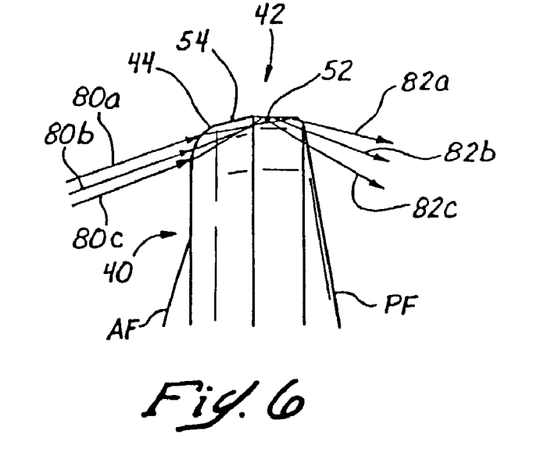
FIG. 6 is an elevational view of a peripheral edge region of the IOL of FIG. 3 showing the paths of a plurality of light rays passing therethrough.

FIG. 6 illustrates a section of the peripheral edge 42 of the optic 40 of FIG. 3 with a plurality of discrete light rays 80a, 80b, 80c, entering the peripheral edge from the anterior side. The refracted/reflected path of each light ray through the peripheral edge 42 is indicated, with the path of each light ray as it exits the peripheral edge 42 indicated as 82a, 82b and 82c.

FIG. 6 thus illustrates the advantageous characteristic of the peripheral edge 42 in diffusing incoming parallel light rays so that the reflected light intensity is reduced. That is, any light that ordinarily would reflect back towards the optical axis at near its original intensity is instead diffused to reduce glare in the IOL. The present invention contemplates utilizing a curved or rounded transition surface, such as the surface 44, in combination with one or more planar edge surfaces that are not parallel to the optical axis, such as the edge surface 54. In the illustrated embodiment, the peripheral edge 42 further includes the edge surface 52 that is substantially parallel to the optical axis. It is believed that the combination of the rounded transition surface 44 on the anterior side leading to the anteriorly-facing edge surface 54 substantially reduces glare within the optic 40.

Figure 7:
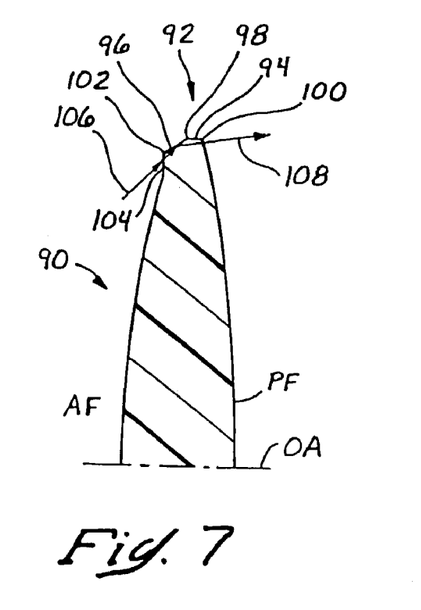
FIG. 7 is a cross-sectional view of a peripheral edge region of an IOL of the present invention having an edge surface that is parallel to the optical axis, an anteriorly-facing edge surface that is not parallel to the optical axis and an anterior peripheral land that is perpendicular to the optical axis.
Figure 8:
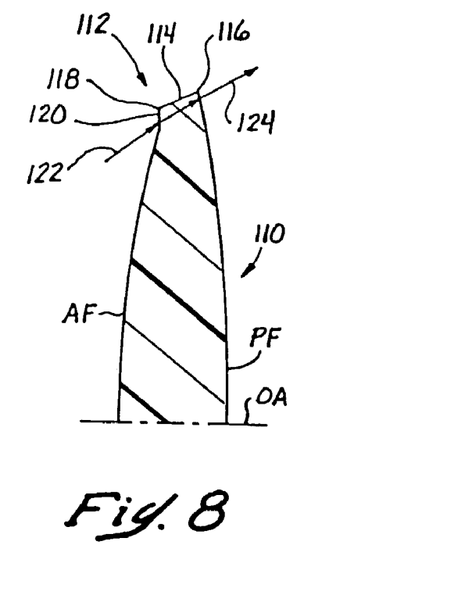
FIG. 8 is a cross-sectional view of a peripheral edge region of an IOL of the present invention having an anteriorly-facing edge surface not parallel to the optical axis and an anterior peripheral land perpendicular to the optical axis.
Figure 9:
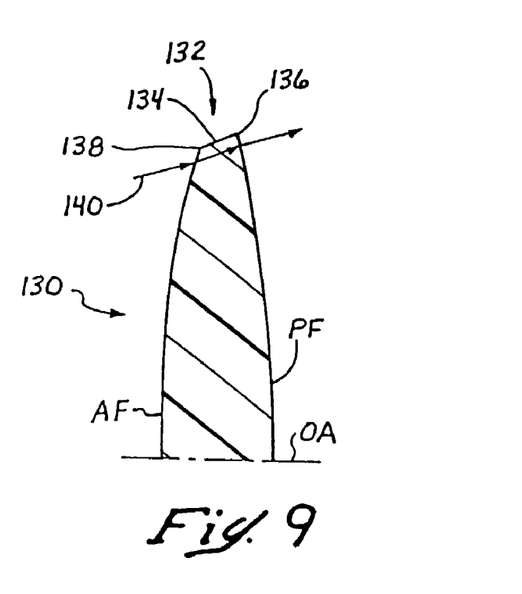
FIG. 9 is a cross-sectional view of a peripheral edge region of an IOL of the present invention having an anteriorly-facing edge surface that is not parallel to the optical axis and no peripheral land.

FIGS. 7–9 each illustrates one half of an optic of an IOL in section having a configuration that reduces glare. In one design, incoming light is refracted so as to decrease the probability of light reflecting off the peripheral edge surfaces toward the optical axis relative to conventional lenses. In another design, incoming light reflects off of an internal peripheral edge surface at a shallow angle of incidence not toward the optical axis so as to decrease the probability of light reflecting off of other edge surfaces relative to conventional lenses. All of the optics disclosed in FIGS. 7–9 comprise an optical axis OA, a convex anterior face AF, and a convex posterior face PF.

An optic 90 seen in FIG. 7 includes a peripheral edge 92 having a first edge surface 94 that is linear and substantially parallel to the optical axis OA, and an anteriorly-facing second edge surface 96 that is linear and non-parallel to the optical axis. With respect to the partial cross-section of the optic 90 seen in FIG. 7, the anteriorly-facing second edge surface 96 is angled in the counter-clockwise (ccw) direction with respect to the optical axis OA. The edge surfaces 94 and 96 meet in the mid-portion of the peripheral edge 92 at a discontinuity 98. A posterior edge corner 100 separates the peripheral edge 92 from posterior face PF, while an anterior edge corner 102 separates the peripheral edge from a peripheral land 104 that is substantially perpendicular to the optical axis.

An incoming light ray 106 is illustrated passing through the peripheral land 104 to reflect off the second edge surface 96 within the optic 90. The resulting reflected ray 108 is deflected through the optic 90 so that it misses the first edge surface 94. In this manner, a substantial portion of the light entering the optic 90 in the region of the peripheral edge 92 is reflected at a relatively shallow angle of incidence off of the second edge surface 96, and is not reflected off the first edge surface 94 toward the optical axis OA. Thus, glare is reduced. To achieve this result, the anteriorly-facing second edge surface 96 is desirably angled at least about 10° with respect to the optical axis OA.

FIG. 8 illustrates an optic 110 having a peripheral edge 112 comprising a single anteriorly-facing edge surface 114 that is linear and non-parallel with respect to the optical axis OA. Thus, the optic 110 has a single conical anteriorly-facing edge surface 114. A posterior edge corner 116 separates the edge surface 114 from the posterior face PF, and an anterior edge corner 118 separates the edge surface 114 from a peripheral land 120 that is substantially perpendicular to the optical axis OA. An incoming light ray 122 is illustrated striking the peripheral land 120 and passing through the optic 110. Because of the anteriorly-facing angle of the edge surface 114, the light ray may refract slightly on passage through the optic 110, as indicated at 124, but will not reflect off the surface edge 114. That is, the posterior edge corner 116 is located farther radially outward from the optical axis OA than the anterior edge corner 118 and a substantial portion of light passing into the region of the peripheral edge 112 simply passes through the material of the optic 110. To achieve this result, the anteriorly-facing edge surface 114 is desirably angled at least about 5° with respect to the optical axis OA.

FIG. 9 illustrates an optic 130 that is substantially similar to the optic 110 of FIG. 8, with a peripheral edge 132 defined by a single anteriorly-facing edge surface 134 that is linear and non-parallel with respect to the optical axis OA. Thus, the optic 130 has a single conical anteriorly-facing edge surface 134. Again, a posterior edge corner 136 separates the peripheral edge 132 from the posterior face PF. An anterior edge corner 138 separates the peripheral edge 132 from the anterior face AF, and there is no anterior peripheral land. The path of a light ray 140 passing through the region of the peripheral edge 132 illustrates the elimination of any reflection off a peripheral edge surface. That is, a substantial portion of light striking the optic 130 from the anterior side simply passes through the optic without reflecting toward the optical axis OA. To achieve this result, the anteriorly-facing edge surface 134 is desirably angled at least about 5° with respect to the optical axis OA.

FIGS. 10–13 illustrate a number of optics of the present invention that are configured to transmit internal light radially outward from their peripheral edges as opposed to reflecting it toward the optical axis. This can be done in a number of ways, all of which result in light hitting the peripheral edge from the interior of the optic at an angle that is less than the critical angle for the refractive index of the lens material. Again, each of the optics in FIGS. 10–13 includes an optical axis OA, a convex anterior face AF, and a convex posterior face PF.

Figure 10:
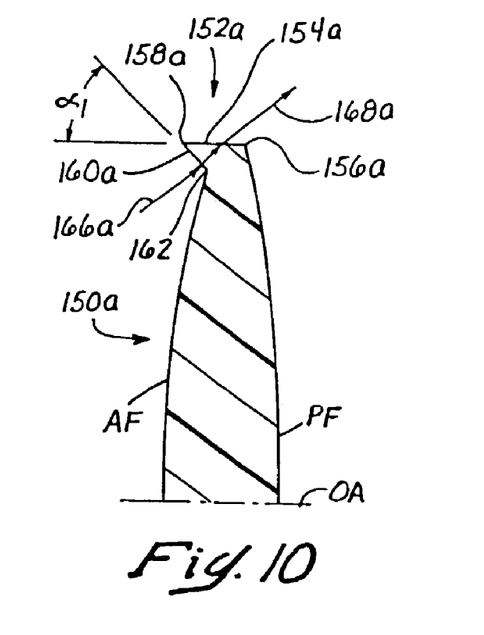
FIG. 10 is a cross-sectional view of a peripheral edge region of an IOL of the present invention having an edge surface that is parallel to the optical axis and an anterior peripheral land that is not perpendicular to the optical axis.
Figure 11:
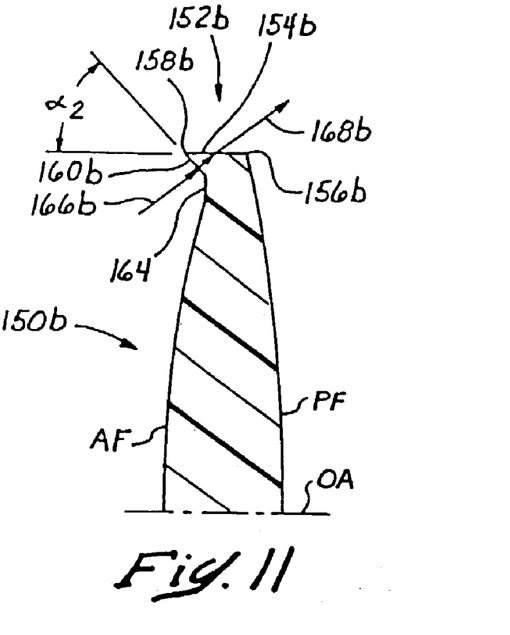
FIG. 11 is a cross-sectional view of a peripheral edge region of an IOL of the present invention having an edge surface that is parallel to the optical axis, an anterior peripheral land that is perpendicular to the optical axis, and an anterior peripheral land that is not perpendicular to the optical axis.

FIGS. 10 and 11 illustrate two substantially similar optics 150a, 150b that will be given corresponding element numbers. Each of the optics 150a, 150b has a peripheral edge 152b, 152b defined by an edge surface 154a, 154b that is linear and substantially parallel to the optical axis OA. A posterior edge corner 156a, 156b separates the edge surface 154a, 154b from the respective posterior face PF. Both optics 150a, 150b include an acute anterior edge corner 158a, 158b separating the edge surface 154a, 154b from an anterior peripheral land 160a, 160b. The peripheral lands 160a, 160b are shown as linear and non-perpendicular with respect to the optical axis OA, but it should be understood that non-linear lands may perform equally as well, and may further diffuse the incoming light. The peripheral land 160a of the optic 150a of FIG. 10 joins with its anterior face AF at a discontinuity 162. On the other hand, a peripheral land 164 that is linear and substantially perpendicular to the optical axis OA joins the peripheral land 160b of the optic 150b of FIG. 11 to its anterior face AF; that is, there are two peripheral lands 160b and 164 on the optic 150b of FIG. 11.

Incoming light rays 166a, 166b are illustrated in FIGS. 10 and 11 striking the respective peripheral lands 160a, 160b and passing through the material of the respective optics 150a, 150b toward the edge surfaces 154a, 154b. Because of the particular angle of the peripheral lands 160a, 160b, the light rays strike the edge surfaces 154a, 154b at angles that are less than the critical angle for the refractive index of the lens material. Therefore, instead of reflecting off of the edge surfaces 154a, 154b, the light rays pass through the peripheral edges 152a, 152b as indicated by the exit rays 168a, 168b. The included angles between the edge surfaces 154a, 154b and the peripheral lands 160a, 160b are shown $\alpha_1$ and $\alpha_2$. These angles are preferably less than 90°, more preferably within the range of about 45° to 88°, and most preferably within the range of about 70° to 88°. Of course, these ranges may differ depending on the refractive index of the material.

Figure 12:
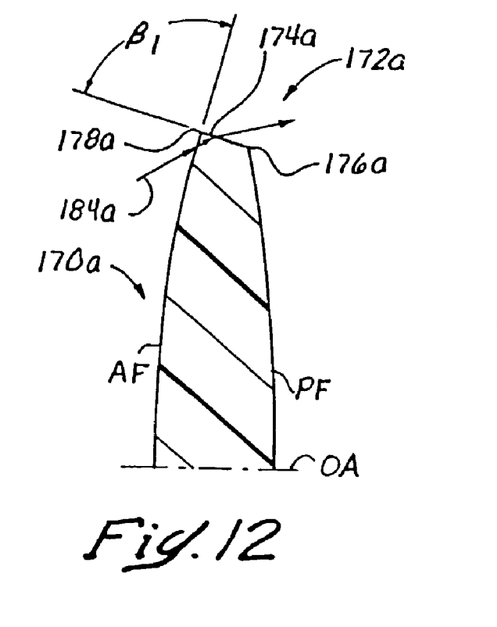
FIG. 12 is a cross-sectional view of a peripheral edge region of an IOL of the present invention having a posteriorly-facing edge surface that is not parallel to the optical axis and no peripheral land.
Figure 13:
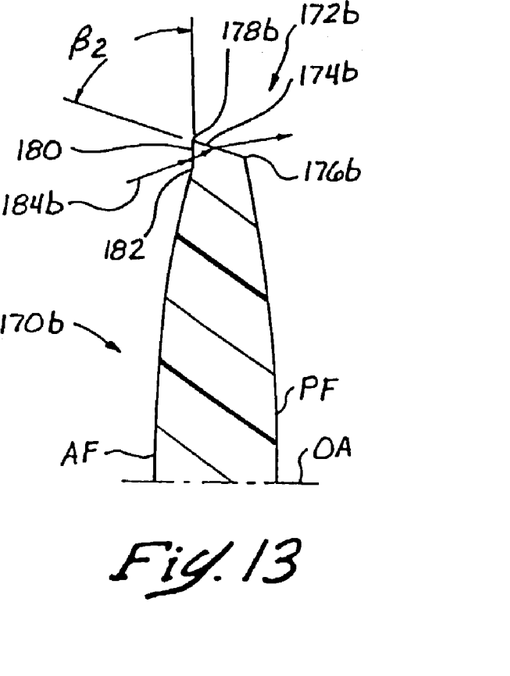
FIG. 13 is a cross-sectional view of a peripheral edge region of an IOL of the present invention having a posteriorly-facing edge surface that is not parallel to the optical axis and an anterior peripheral land that is perpendicular to the optical axis.

FIGS. 12 and 13 illustrate similar optics 170a, 170b that each have a peripheral edge 172a, 172b defined by a posteriorly-facing edge surface 174a, 174b that is linear and non-parallel with respect to the optical axis OA. A posterior edge corner 176a, 176b separates the edge surface 174a, 174b from the posterior face PF. On the optic 170a of FIG. 12, an anterior edge corner 178a separates the edge surface 174a from the anterior face AF, without a peripheral land. In contrast, as seen in FIGS. 13 an anterior edge corner 178b separates the edge surface 174b from a peripheral land 180 that is linear and substantially perpendicular to the optical axis OA of the optic 170b. The peripheral land 180 meets the anterior face AF at a discontinuity 182.

The angles of the anterior edge corners 178a and 178b are indicated at $\beta_1$ and $\beta_2$. The magnitude of the angle $\beta_1$ depends both on the convexity of the anterior face AF and the angle of the posteriorly-facing edge surface 174a with respect to the optical axis OA. The anterior face AF may have widely differing convexities, but desirably the posteriorly-facing edge surface 174a is at least 2° (clockwise in the drawing) with respect to the optical axis OA. Therefore, the angle $\beta_1$ is preferably less than about 120°, and more preferably are within the range of about 70° to 120°. The magnitude of the angle $\beta_2$ seen in FIG. 13 depends both on the angle of the peripheral land 180 and the angle of the posteriorly-facing edge surface 174b with respect to the optical axis OA. The peripheral land 180 is shown as linear and perpendicular with respect to the optical axis OA, but it should be understood that non-linear and non-parallel lands may perform equally as well. Desirably the posteriorly-facing edge surface 174b is at least 2° (clockwise in the drawing) with respect to the optical axis OA. Therefore, the angle $\beta_2$ is preferably acute, and more preferably is within the range of about 30° to 88°. Of course, these ranges may differ depending on the refractive index of the material.

FIGS. 12 and 13 illustrate incoming light rays 184a, 184b that strike the anterior side of the respective optic 170a, 170b adjacent the peripheral edges 172a, 172b and subsequently pass through the material of the optic and through the edge surfaces 174a, 174b without reflection. Again, this phenomenon is caused by the angles at which the light rays strike the edge surfaces 174a, 174b, which are lower than the critical angle for the refractive index of the lens material. As a result, the light rays simply pass through the peripheral edges 172a, 172b without reflecting back towards the optical axis OA.

Figure 14A:
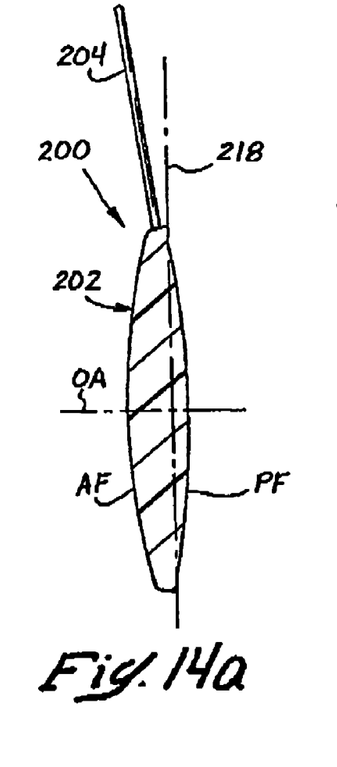
FIG. 14a is a radial sectional view of an IOL of the present invention showing a fixation member extending from a peripheral edge.
Figure 14B:
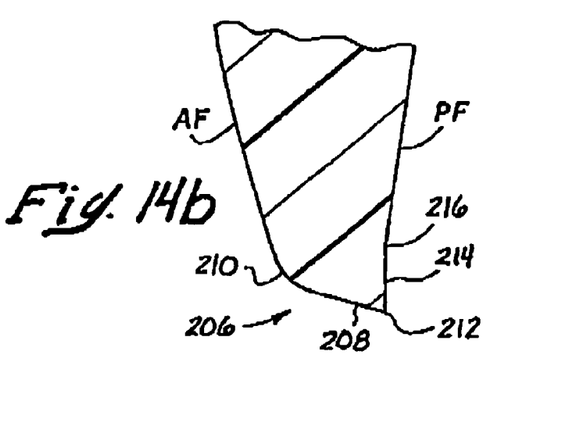

FIG. 14a illustrates a further embodiment of an IOL 200 of the present invention having an optic 202 and a plurality of fixation members 204 extending radially outward therefrom, only one of which is shown. FIG. 14b is an enlargement of a peripheral edge region of the optic 202. As always, the optic 202 includes an optical axis OA, a convex anterior face AF, and a convex posterior face PF.

With reference to FIG. 14b, the optic 202 includes a peripheral edge 206 defined by an anteriorly-facing edge surface 208 that is linear and non-parallel with respect to the optical axis OA. A curved or rounded transition surface 210 smoothly blends the linear edge surface 208 to the convex anterior face AF. An acute posterior edge corner 212 separates the edge surface 208 from a peripheral land 214 that is linear and substantially perpendicular to the optical axis OA. The peripheral land 214 joins with the convex posterior face PF at a discontinuity 216. FIG. 14a illustrates a plane 218 coincident with the circular posterior edge corner 212. This plane represents a separation line between two mold halves used to form the optic 202. In this manner, the acute peripheral edge corner 212 can be easily formed between the mold halves.

The embodiment shown in FIGS. 14a and 14b incorporates a combination of several advantageous features previously described. That is, the rounded transition surface 210 tends to diffuse light rays entering from the anterior side, as described above with respect to the embodiment of FIGS. 3–5. In addition, the edge surface 208 is angled in such a manner that some of the light passing through the transition surface 210 will not even strike it, and the light that does will be reflected at a relatively shallow angle of incidence that reduces glare.

Figure 15:
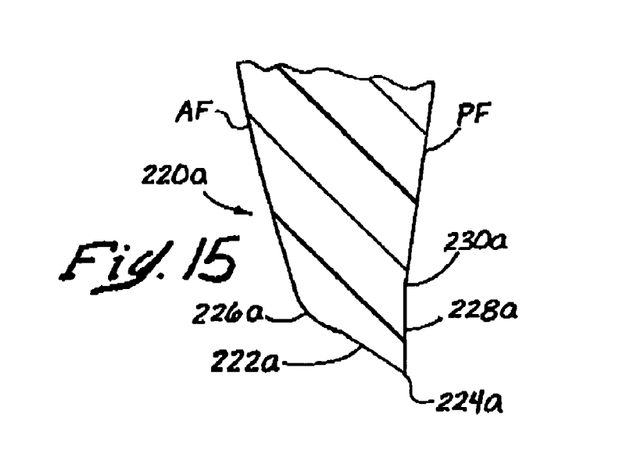
FIGS. 15–17 are elevational views of peripheral edge regions of IOLs of the present invention each having an anteriorly-facing edge surface that is not parallel to the optical axis, a rounded transition surface between the edge surface and the anterior face of the IOL, and a posterior peripheral land.
Figure 16:
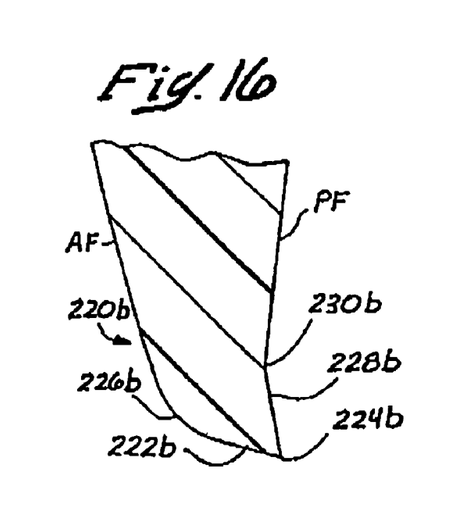
Figure 17:
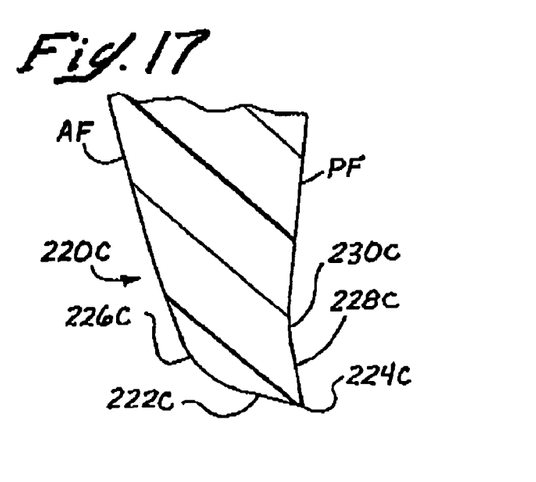

FIGS. 15–17 illustrate the peripheral edges of three optics 220a, 220b, 220c having similar shapes. The optic 220a of FIG. 15 has a peripheral edge defined by an anteriorly-facing surface 222a that is linear and non-parallel with respect to the optical axis, an acute posterior edge corner 224a, and a rounded anterior transition surface 226a blending with the anterior face AF. A peripheral land 228a that is generally perpendicular with respect to the optical axis extends between the posterior face PF and the edge corner 224a, and joins with the posterior face PF at a discontinuity 230a. The included angle between the surface 222a and the peripheral land 228a is relatively small, and the rounded transition surface 226a protrudes slightly outward from the surface 222a.

The peripheral edge of the optic 220b shown in FIG. 16 also includes an anteriorly-facing surface 222b that is linear and non-parallel with respect to the optical axis, an acute posterior edge corner 224b, and a rounded anterior transition surface 226b blending with the anterior face AF. A peripheral land 228b that is not perpendicular to the optical axis extends between the posterior face PF and the edge corner 224b. The peripheral land 228b joins with the posterior face PF at a discontinuity 230b. The included angle between the surface 222b and the peripheral land 228b is slightly larger than that shown in FIG. 15, primarily because the surface 222b has a shallower angle with respect to the optical axis than the surface 222a.

The peripheral edge of the optic 220c shown in FIG. 17 also includes an anteriorly-facing surface 222c that is linear and non-parallel with respect to the optical axis, an acute posterior edge corner 224c, and a rounded anterior transition surface 226c blending with the anterior face AF. A peripheral land 228c that is not perpendicular to the optical axis extends between the posterior face PF and the edge corner 224c. The peripheral land 228c joins with the posterior face PF at a discontinuity 230c. The optic 220c is fairly similar to the optic 220b, but has a slightly less convex posterior face PF.

Figures 18, 19, 20:
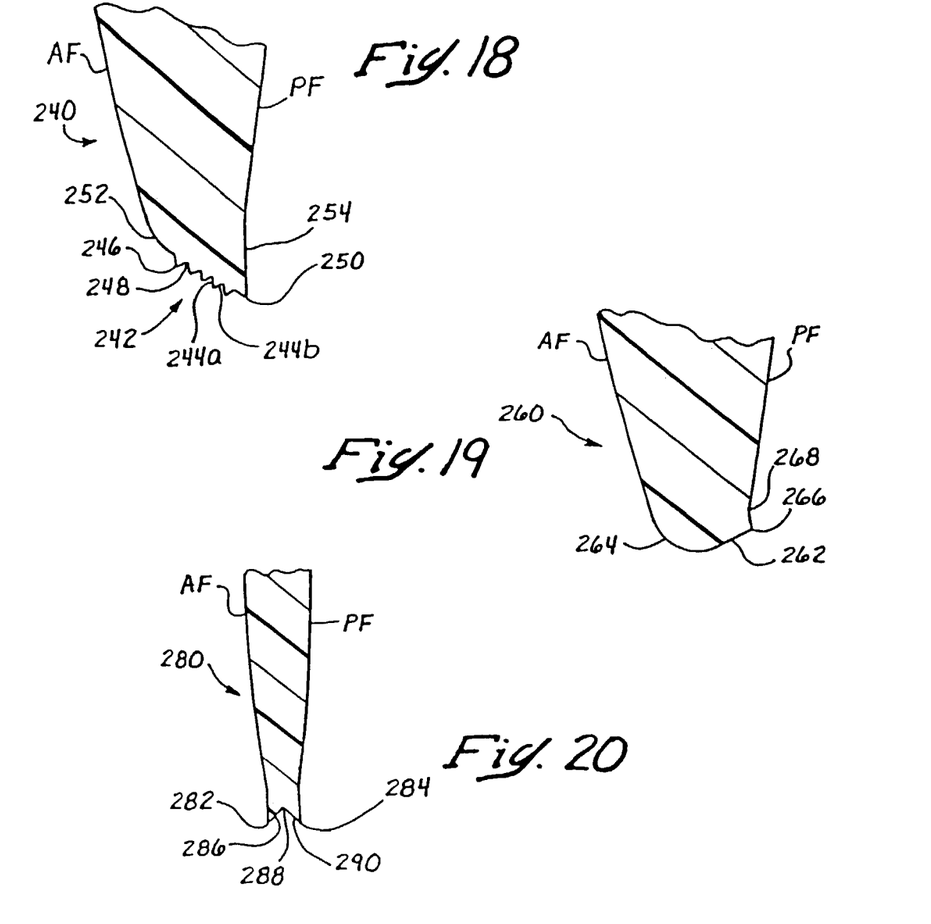
FIG. 18 is an elevational view of a peripheral edge region of an IOL of the present invention having a baffle structure disposed along an anteriorly-facing edge surface.
FIG. 19 is an elevational view of a peripheral edge region of an IOL of the present invention having an anteriorly-facing edge surface and a rounded transition surface between the edge surface and the anterior face of the IOL.
FIG. 20 is an elevational view of a peripheral edge region of an IOL of the present invention having both anteriorly- and posteriorly-facing edge surfaces.

FIG. 18 illustrates the peripheral edge of an optic 240 having a saw-tooth or baffled edge surface 242. The edge surface 242 is generally aligned to face the anterior side of the optic 240 and includes multiple tooth facets or surfaces 244a and 244b defining peaks 246 and troughs 248. Each tooth surface 244a is desirably parallel to the other surfaces on the same side of each tooth, as is each tooth surface 244b with respect to the others on the other side of each tooth. The peripheral edge of the optic 240 further includes a posterior edge corner 250 and a rounded transition surface 252 blending into the anterior face AF. A peripheral land 254 that is generally perpendicular to the optical axis extends between the posterior face PF and the edge corner 250.

Still with reference to FIG. 18, light striking the peripheral edge of the optic 240 from the anterior side is scattered and diffused upon passage through the baffled edge surface 242 and the rounded transition surface 252. This helps reduce glare within the optic 240. In addition, the edge surface 242 is angled so as to be non-parallel with respect to the optical axis, and thus some of the light rays internal to the optic 240 will not even strike this edge surface to further reduce glare.

An optic 260 that includes a linear posteriorly-facing edge surface 262 is seen in FIG. 19. The peripheral edge of the optic 260 comprises the edge surface 262, a rounded transition surface 264 blending to the anterior face AF, and a peripheral edge corner 266 adjacent a short peripheral land 268. The advantages of the posteriorly-facing edge surface 262 were described previously with respect to FIGS. 12 and 13, and primarily involved light being transmitted through the edge surface as opposed to being internally reflected off of it. Of course, light that is transmitted through the edge surface 262 as opposed to being reflected off of it cannot contribute to glare. In addition, the rounded transition surface 264 helps to diffuse light rays striking the peripheral edge, thus further reducing glare.

FIG. 20 illustrates an optic 280 having both an anterior edge corner 282 and posterior edge corner 284. A posteriorly-facing edge surface 286 extends from the anterior edge corner 282 to an apex 288, and an anteriorly-facing edge surface 290 extends between the apex and the posterior edge corner 284. The apex 288 defines the midpoint of a groove, and the resulting configuration in cross-section is something like a forked-tongue. A pair of peripheral lands 292a, 292b extends between the edge corners 282, 284 and the respective anterior and posterior faces of the optic 280. The peripheral lands 292a, 292b are desirably perpendicular to the optical axis. Again, the provision of linear edge surfaces that are non-parallel with respect to the optical axis helps reduce glare within the optic 280. Furthermore, the relatively sharp edge corners 282, 284 helps reduce PCO by inhibiting cell growth on both the anterior and posterior sides of the optic 280.

Figure 21:
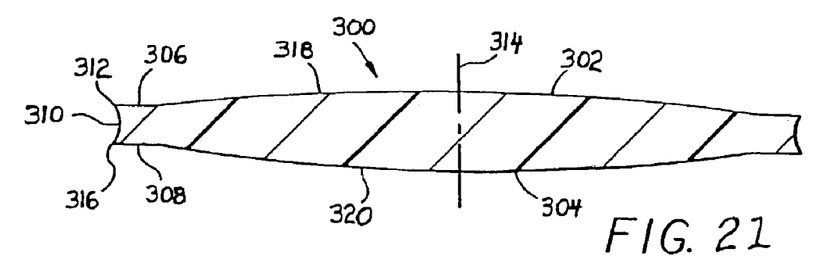
FIG. 21 is a cross-sectional view of the optic of an alternative IOL of the present invention.

Another embodiment of the invention seen in FIG. 21 has an optic 300 with an anterior face 302, a posterior face 304, an anterior peripheral region 306, a posterior peripheral region 308 and a peripheral edge surface 310. The peripheral edge surface 310 has a continuously curved, concave configuration, for example, in cross-section. The peripheral edge surface 310 intersects anterior peripheral region 306 at anterior peripheral corner edge 312 at an angle of about 70°. Corner edge 312 is at a discontinuity between anterior face 302 (anterior peripheral region 306) and peripheral edge surface 310, and circumscribes optical axis 314. Peripheral edge surface 310 intersects posterior peripheral region 308 at posterior peripheral corner edge 316 at an angle of about 70° Corner edge 316 is at a discontinuity between posterior face 304 (posterior peripheral region 308) and peripheral edge surface 310, and circumscribes optical axis 314.

The anterior and posterior peripheral regions 306 and 308 extend radially inwardly, for example, for a distance of about 0.1 mm to about 1.0 mm or more (about 0.5 mm as shown in FIG. 21), from the peripheral edge surface 310, and peripheral corner edge 312 and 316 respectively, and are substantially planar, more particularly, substantially perpendicular to the optical axis 314 of optic 300. Anterior face 302 includes an additional anterior region 318 which is convex, not planar. Posterior face 304 includes an additional posterior region 320 which also is convex, not planar. The dimension of optic 300 between anterior face 302 and posterior face 304 at the peripheral regions 306 and 308 is smaller than the same dimension at the optical axis 314.

It is found that implanting an IOL having the optic 300 in the capsular bag of an eye effectively inhibits or retards cell migration or growth, for example, epithelial cell migration or growth, from the eye onto and/or over the anterior and posterior faces 302 and 304 of optic 300. In addition, it is found that a reduced amount of edge glare is obtained with an IOL having the optic 300 implanted in the capsular bag of the eye.

Without wishing to limit the invention to any particular theory of operation, it is believed that an IOL having the optic 300 provides for inhibition of cell migration or growth onto and/or over the optic 300 because of the sharp or abrupt peripheral corner edges 312 and 316. Thus, it is believed that the cells from the eye have a reduced tendency to grow onto and/or over the anterior face 302 and posterior face 304 relative to a substantially identical IOL without such peripheral corner edge. In addition, it is believed that the reduced glare obtained using an IOL having the optic 300 results from the curved configuration of the peripheral edge surface 310. Thus, an IOL having the optic 300 including the substantially continuously curved peripheral edge surface 310 provides reduced glare relative to a substantially similar IOL having a peripheral edge surface which is substantially parallel, for example, in cross-section, to the optical axis of the IOL.

Figure 22:
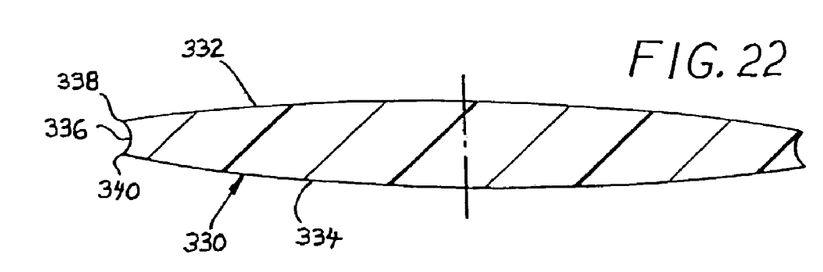
FIG. 22 is a cross-sectional view of the optic of an alternate embodiment of an IOL in accordance with the present invention.

FIG. 22 illustrates an alternate embodiment of an IOL in accordance with the present invention. This IOL has an optic shown generally at 330. Except as expressly described herein, optic 330 is structured and functions similarly to optic 300.

The principal difference between the optic 330 and the optic 300 relates to the shape of the anterior face 332 and the shape of posterior face 334. Specifically, anterior face 332 is convex throughout, and optic 330 does not include a substantially planar anterior peripheral region. This convex anterior face 332 intersects peripheral edge surface 336 at sharp anterior peripheral corner edge 338. Similarly, posterior face 334 is convex throughout, and optic 330 does not include a substantially planar posterior peripheral region. This convex posterior face 334 intersects peripheral edge surface 336 at sharp posterior peripheral corner edge 340. The specific configuration of anterior face 332 and posterior face 334 can be independently provided to address the needs of any given specific application including the following factors; the vision correction or corrections desired, the size of optic 330, the size of the eye in which an IOL having optic 330 is to be placed and the like factors. Optic 330 inhibits or retards cell migration or growth and provides a reduced amount of edge glare as does the optic 300, described above.

Figure 23:
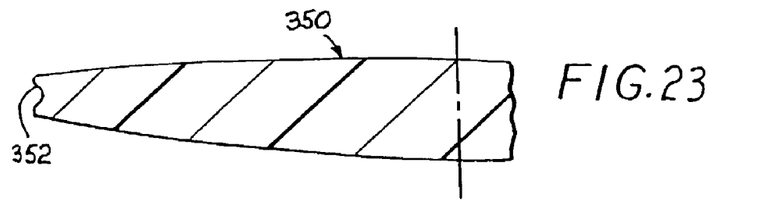
FIG. 23 is a partial cross-sectional view of the optic of a further embodiment of an IOL in accordance with the present invention.

FIG. 23 illustrates a further embodiment of an IOL in accordance with the present invention. This IOL has an optic shown generally at 350. Except as expressly described herein, optic 350 is structured and functions similarly to optic 330.

The principal difference between optic 350 and optic 330 relates to the shape of peripheral edge surface 352. Specifically, the curvature of peripheral edge surface 352 is more complex relative to the curvature of peripheral edge surface 336. In particular, the curvature of edge surface 352 varies substantially continuously while the curvature of edge surface 336 is a substantially constant concave arc (in cross-section). Peripheral edge surface 352 is configured to reduce the amount of edge glare obtained with optic 350 in the eye relative to, for example, IOL 30 of FIG. 2. The specific configuration or curvature of peripheral edge surface 352 is provided to address the needs of a specific application, including the following factors: the size of the optic 350, the size of the eye in which an IOL having the optic 330 is to be placed and the like factors.

Figure 24:
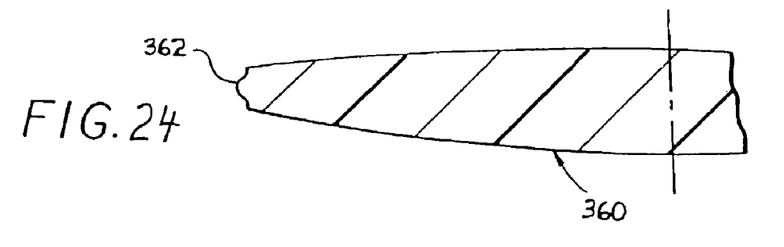
FIG. 24 is a partial cross-sectional view of an additional embodiment of an IOL in accordance with the present invention.

FIG. 24 illustrates an additional embodiment of the present invention. The IOL illustrated in FIG. 24 has an optic shown generally at 360. Except as expressly described herein, optic 360 is structured and functions similarly to optic 330.

The primary difference between optic 360 and optic 330 relates to the configuration of peripheral edge surface 362. Specifically, the curvature of peripheral edge surface 362 varies substantially continuously (in a manner which is substantially the reverse of the curvature of peripheral edge surface 352 of optic 350) while the curvature of edge 336 is a substantially constant concave arc (in cross-section). The peripheral edge surface 362 of optic 360 is effective in reducing the glare caused by the presence of optic 360 in the eye relative to the glare obtained with IOL 30 of FIG. 2 in the eye.

Figure 25:
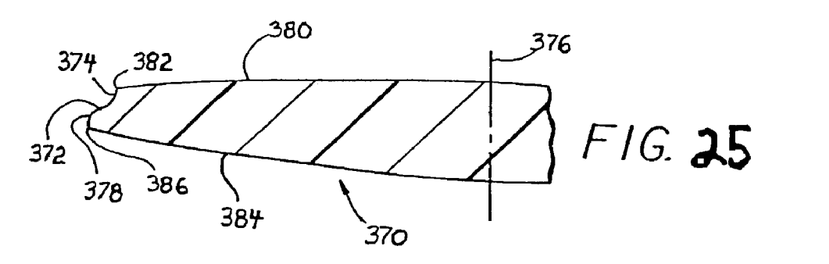
FIG. 25 is a partial cross-sectional view of the optic of another embodiment of an IOL in accordance with the present invention.

FIG. 25 illustrates an additional embodiment of an IOL in accordance with the present invention. Except as expressly described herein, this IOL, having an optic shown generally at 370 is structured and functions similarly to optic 330.

The primary difference between optic 370 and optic 330 relates to the configuration of the peripheral edge surface 372. Specifically, peripheral edge surface 372 includes a first portion 374 which is concave relative to the optical axis 376 of optic 370. Peripheral edge surface 372 also includes a second portion 378 which is convex relative to the optical axis 376 of optic 370. Thus, the curvature of the peripheral edge surface of the present IOLs, for example, peripheral edge surface 372 of optic 370, can be relatively complex. Peripheral edge surface 372 is effective to provide reduced glare in the eye relative to IOL 30 of FIG. 2. In addition, it should be noted that the peripheral edge surface 372 intersects anterior face 380 at anterior peripheral corner edge 382 at an angle of about 90°. Similarly, the peripheral edge surface 372 intersects posterior peripheral region 384 at posterior peripheral corner edge 386 at an angle of about 90°.

Optic 370, as with all of the IOLs in accordance with the present invention, is effective in inhibiting or retarding cell migration or growth from the eye onto or over the optic 370.

Figure 26:
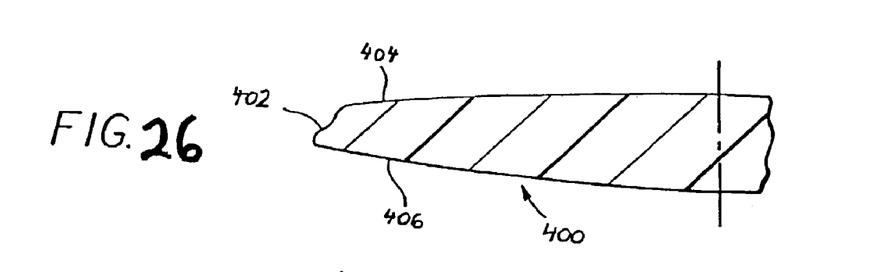
FIG. 26 is a partial cross-sectional view of the optic of a further alternate embodiment of an IOL in accordance with the present invention.

FIG. 26 illustrates a further alternate embodiment of an IOL in accordance with the present invention. This IOL has an optic shown generally at 400. Except as expressly described herein, optic 400 is structured and functions substantially similarly to optic 330.

The primary differences between optic 400 and optic 330 relate to the configuration of peripheral edge surface 402 and the configuration of the intersection between anterior face 404 and peripheral edge surface 402 of optic 400. Specifically, peripheral edge surface 402 has a continuously curved configuration somewhat similar to peripheral edge surface 372 of optic 370. Also, the anterior face 404 intersects peripheral edge surface 402 on a curve (that is on a continuity not at a discontinuity). In other words, the intersection of anterior face 404 and peripheral edge surface 402 is smooth or continuous, not sharp or discontinuous.

Optic 400 is effective in reducing the amount of glare obtained with optic 400 in the eye relative to IOL 30 of FIG. 2 in the eye. Also, optic 370 is effective in retarding or inhibiting migration from the eye onto and/or over cell growth or migration from the eye onto and/or over the posterior face 406 of optic 400.

Figure 27:
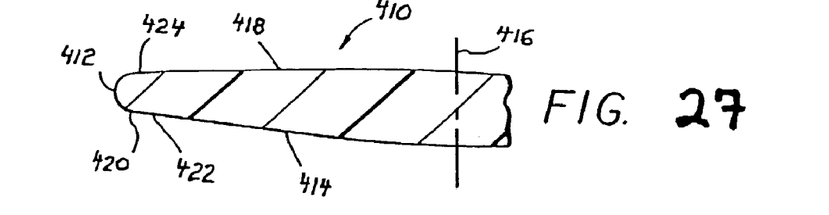
FIG. 27 is a partial cross-sectional view of the optic of a still further embodiment of an IOL in accordance with the present invention.

FIG. 27 illustrates a still further embodiment of an IOL in accordance with the present invention. Except as expressly described herein, this IOL, having an optic shown generally at 410 is structured and functions similarly to optic 330.

The primary difference between optic 410 and optic 330 relates to the configuration of the peripheral edge surface 412 and to the configuration of posterior face 414. Specifically, peripheral edge surface 412 is convex relative to the optical axis 416 of optic 410. Peripheral edge surface 412 does not intersect anterior face 418 at a sharp or discontinuous corner edge, but does intersect posterior face 414 at an obtuse angle at posterior peripheral corner 420. Posterior face 414 includes a peripheral region 422 which is substantially perpendicular to optical axis 416. Anterior face 418 includes a peripheral region 424 which is roughened to be at least partially opaque to the transmission of light. The combination of the convex peripheral edge surface 412 and the at least partially opaque peripheral region 424 is particularly effective in reducing glare, for example, from corner 420, obtained with an IOL having optic 410 in the eye.

Figure 28:
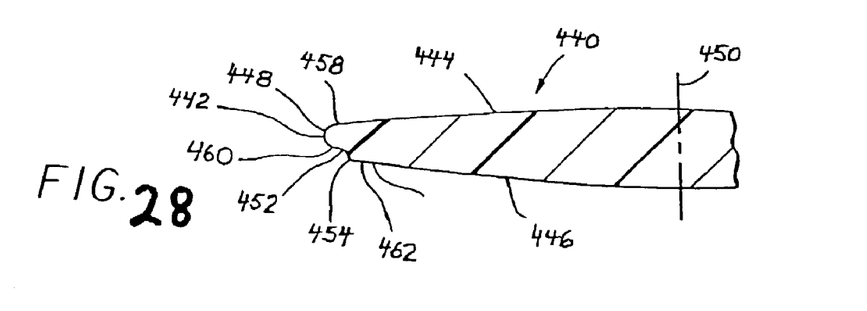
FIG. 28 is a partial cross-sectional view of the optic of still another embodiment of an IOL in accordance with the present invention.

FIG. 28 illustrates still another embodiment of an IOL in accordance with the present invention. This IOL has an optic shown generally at 440. Except as expressly described herein, optic 440 is structured and functions substantially similarly to optic 330.

The primary differences between optic 440 and optic 330 relate to the configuration of peripheral edge surface 442, the configuration of the intersection between anterior face 444 and peripheral edge surface 442 of optic 440 and the configuration of posterior face 446. Peripheral edge surface 442 includes a first portion 448 which is convex relative to optic axis 450 of optic 440. Peripheral edge surface 442 also includes a second portion 452 which transitions from first portion 448 and intersects posterior face 446 at corner 454. Peripheral edge surface 442 does not intersect anterior face 444 at a sharp or discontinuance corner edge. Posterior face 446 includes a peripheral region 456 which is substantially perpendicular to optical axis 450. Anterior face 444 includes the peripheral region 458 which is roughened to be at least partially opaque to the transmission of light. Region 460 of peripheral edge surface 442 and region 462 of posterior face 446 are also roughened to be at least partially opaque to the transmission of light. The combination of the peripheral edge surface 442 and the at least partially opaque regions 458, 460, 462 is particularly effective in reducing glare, for example, from corner edge 454, obtained with optic 440 in the eye.

In addition to designing the geometry of the peripheral edge of the intraocular lenses of the present invention to reduce glare and posterior capsule opacification (PCO), the edges and surfaces near the edges may be "textured" or frosted to cause scatter of light impinging on the peripheral region. Such scattering helps reduce edge glare. In addition, use of texture in combination with various edge geometries may help reduce PCO. Various texturing regimens may be used, as described in U.S. Pat. No. 5,693,094, entitled IOL for Reducing Secondary Opacification, hereby expressly incorporated by reference. With respect to specific embodiments, IOLs made of silicone desirably include texturing/frosting on at least one edge surface as well as on a peripheral region of the posterior face, or intermediate land. Acrylic IOLs, on the other hand, desirably include texturing/frosting on at least one edge surface, and preferably on an edge surface that is parallel to the optical axis.

The intraocular lenses of the present invention may be manufactured using a variety of techniques, including injection molding, compression molding, lathing, and milling. Those of skill in the art will understand how to form the mold dies, or program the cutting tools to shape the lenses in accordance with present invention. Importantly, care must be taken to avoid rounding the various corners or discontinuities for the particular optic during the polishing process. Therefore, the corners must be masked or otherwise protected while the lens is being polished. Alternatively, the unmasked lens may be polished and then the various edge surfaces re-cut to insure sharp corners.

With reference back to FIG. 1, the design of the fixation members 24a, 24b may play an important role in reducing the risk of PCO for any particular lens. That is, the fixation members 24a, 24b must be designed such that during capsular contraction, there is enough axial movement and accompanying bias of the lens against the posterior capsule to seal the capsule around the posterior edge corners of the lens. A variety of fixation members 24a, 24b are known in the art that can provide the required posterior bias to the lens. The precise configuration of the fixation members 24a, 24b may vary depending on the overall lens diameter, the diameter of the optic, the angle of the fixation member, the stiffness of the fixation member material, the gauge of the fixation member, the geometry of the fixation member, and the way in which the fixation member is attached to the lens.

The present invention very effectively provides IOLs which inhibit cell growth or migration, in particular epithelial cell growth or migration from a capsular bag, onto and/or over the IOL optics. In addition, the IOLs produce reduced glare, in particular edge glare, relative to a lens having a peripheral edge which is substantially parallel, in cross-section, to the optical axis of the IOL optic. These benefits are achieved with IOLs which are easily manufactured and inserted in the eye. Such IOLs can be made of any suitable material, and provide effective performance and substantial benefits to the patient.

While this invention has been described with respect to various specific examples and embodiments, it is to be understood that the invention is not limited thereto and that it can be variously practiced within the scope of the following claims.

What is claimed is:

1. An intraocular lens that inhibits cell growth thereon and reduces glare from incoming light rays, comprising:
   a centered optic sized and adapted for placement in the capsular bag of an eye and shaped to direct light toward the retina of the eye, the optic having a central optical axis, an anterior face and an opposed posterior face, and a peripheral edge between the anterior and posterior faces and circumscribing the optic, the peripheral edge comprising:
   a linear edge surface;
   a non-discontinuous convex portion smoothly blending the anterior face with the linear edge surface and having a curvature substantially greater than the curvature of the anterior face on the peripheral edge for reducing glare from incoming light rays; and
   a peripheral corner edge located at a discontinuity between the linear edge surface and the posterior face for inhibiting cell growth onto the optic.

2. The intraocular lens of claim 1, wherein the anterior face has a substantially constantly curved corrective portion centered on the optical axis and the optic further includes an anterior peripheral region between the corrective portion and the non-discontinuous convex portion of the peripheral edge.

3. The intraocular lens of claim 2, wherein the anterior peripheral region is substantially planar and perpendicular to the central optical axis.

4. The intraocular lens of claim 2, wherein the anterior peripheral region is at least partially opaque to the transmission of light to help reduce glare from incoming light rays.

5. The intraocular lens of claim 1, wherein the discontinuity between the peripheral edge and posterior face is formed where the peripheral edge and the posterior face intersect at an angle in a range of about 45° to about 135°.

6. The intraocular lens of claim 5, wherein the peripheral edge and the posterior face intersect at an angle in a range of about 60° to about 120°.

* * * * *